United States Patent [19]

Alexander et al.

[11] Patent Number: 4,847,298

[45] Date of Patent: Jul. 11, 1989

[54] ACYLCARNITINES AS ABSORPTION-ENHANCING AGENTS FOR DRUG DELIVERY THROUGH MUCOUS MEMBRANES OF THE NASAL, BUCCAL, SUBLINGUAL AND VAGINAL COMPARTMENTS

[75] Inventors: Jose Alexander; Joseph A. Fix; A. J. Repta, all of Lawrence, Kans.

[73] Assignee: Merck & Co., Inc., Rahway, N.J.

[21] Appl. No.: 130,919

[22] Filed: Dec. 10, 1987

Related U.S. Application Data

[62] Division of Ser. No. 766,378, Aug. 16, 1985, Pat. No. 4,731,360.

[51] Int. Cl.[4] .......................................... A61K 31/195

[52] U.S. Cl. ................................... 514/565; 514/567; 514/946; 514/947

[58] Field of Search ............... 514/567, 562, 565, 946, 514/947

[56] References Cited

U.S. PATENT DOCUMENTS 4,352,800 10/1982 Kamada .............................. 519/946

Primary Examiner—Frederick E. Waddell
Attorney, Agent, or Firm—Manfred Polk; Michael C. Sudol

[57] ABSTRACT

Acylcarnitine used as a nasal, buccal, sublingual and vaginal drug absorption enhancing vehicle for poorly absorbed drugs.

12 Claims, No Drawings

ACYLCARNITINES AS ABSORPTION-ENHANCING AGENTS FOR DRUG DELIVERY THROUGH MUCOUS MEMBRANES OF THE NASAL, BUCCAL, SUBLINGUAL AND VAGINAL COMPARTMENTS

CROSS REFERENCE TO RELATED APPLICATIONS

This is a divisional application of U.S. Ser. No. 766,378 filed Aug. 16, 1985 now U.S. Pat. No. 4,731,360.

BACKGROUND OF THE INVENTION

The invention relates to a novel method and compositions for enhancing absorption of poorly absorbed drugs from the nasal, buccal, sublingual and vaginal compartments by incorporating therein an acylcarnitine absorption enhancing agent. The use of acylcarnitines to promote nasal, buccal, sublingual and vaginal drug absorption offers several advantages over attempts to increase drug absorption from the gastrointestinal tract. Namely, the compounds are not exposed to the enzymatic activities of the stomach and small intestine, and are not presented to the acidic environment of the stomach. This can offer significant advantages in terms of drug stability.

DESCRIPTION OF THE PRIOR ART

Although numerous references describe carnitine-acylcarnitine translocase system in mitochondria, the instant use of acylcarnitines to promote drug absorption through the mucous membranes of the nasal, buccal, sublingual and vaginal compartments constitutes a novel and unobvious use of said acylcarnitine compounds. The carnitine-acylcarnitine translocase system has been localized in skeletal muscle, cardiac muscle, epididymal tissue, liver, kidney and brain. Evidence for the existence of this system in the non-muscle mucosal cells of the nasal, buccal, sublingual and vaginal compartments, which is the barrier to drug absorption, has not been found. The system is located on the inner membrane of the mitochondria, an intracellular organelle and its functions are to transport fatty acids across the mitochondria membrane and lead to intraorganelle concentration and oxidation of the fatty acids. There is no evidence to indicate that acylcarnitines will promote transmembrane movement of another target molecule. Carnitine can transverse membranes, however, carnitine alone has no effect in the instant application. The acylcarnitine ester is required for the absorption promoting effect. Thus, the intramitochondrial transport of fatty acids, which is a known function of carnitine, is unrelated to its function as a mucous-membrane drug absorption promoter.

Acylcarnitines have previously been shown to increase drug absorption when administered to the small intestine or rectum. However, the barrier membranes present in the nasal, oral and vaginal cavities are significantly different than that observed in the intestine or rectum. The non-intestinal barrier membranes of the instant application are primarily stratified squamous epithelium, rather than the columnar absorptive cells of the intestine and rectum. The nasal, oral and vaginal cavities also offer a much reduced absorptive surface area. The enzymatic activity of the fluid secretions can also be significantly different. Based on the different structural and absorptive properties of the various mucous membranes, the use of acylcarnitines as drug absorption enhancing agents in nasal, buccal, sublingual and vaginal applications is a non-obvious approach to systemic drug delivery.

The use of acylcarnitines to promote nasal, buccal, sublingual and vaginal drug absorption affords several advantages over the prior art's non-related absorption promoting compounds. The acylcarnitines, especially these with medium and long chain fatty acid components, are more potent than the presently used absorption promoting agents. As an example, in aqueous solutions, the acylcarnitines are effective absorption promoting agents at levels as low as 0.05%. By contrast, the effective dose of other known absorption promoters is significantly higher: polyacrylic acid gel—1%, surfactants—1%. This difference in potency affords opportunities for reducing the required size of the dosage form and potentially minimizing side effects. The acylcarnitines cause reversible changes in mucosal membrane permeability to the target drug, indicating that a permanent change has not occured. Other promoting agents, such as the surfactants, cause a relatively permanent change in permeability, which is only overcome by turnover of the mucosal cells, a process which may require days for completion. Another potential advantage of the acylcarnitines is that, unlike chelating agent such as EDTA, the acylcarnitines may not necessarily sequester divalent cations ($Mg^{++}$ or $Ca^{++}$) which are necessary for the normal functioning of cells. In other words, there is no tissue damage at concentrations of acylcarnitines which significantly increase drug absorption. In contrast to this, studies have indicated that surfactant activity, as with sodium lauryl sulfate, is generally associated with some degree of cellular damage. This lack of tissue damage affords a significant advantage to the use of acylcarnitines in promoting drug absorption which can be metabolized through normal pathways in the body. This eliminates a potential problem from introducing substances which are not normally present in the biochemical pathways of the body.

SUMMARY OF THE INVENTION

It has been found that when poorly absorbed drugs are administered in the nasal, buccal, sublingual or vaginal cavity, the bioavailability of said drugs is increased by administering together with an acylcarnitine absorption enhancing agent.

Accordingly, it is an object of this invention to enhance the bioavailability of poorly absorbed drugs administered by the nasal, buccal, sublingual or vaginal route by administering therewith an acylcarnitine absorption enhancing agent.

It is an object of the invention to provide a stable drug form utilizing a novel class of acylcarnitine agent which when administered nasally, buccally, sublingually or vaginally will provide an increased blood level of the therapeutic agent.

Another object of the invention is to provide an acylcarnitine absorption promoter of mucous membrane drug absorption at concentrations which do not alter the normal morphology of the mucosal cells.

Still another object of the invention is to provide an acylcarnitine series of absorption-enhancing agents that are endogenous and can be metabolized through normal pathways available in the body.

Other objects, features and advantages of the invention will be apparent to those skilled in the art from the detailed description of the invention which follows.

All of the foregoing objects are readily attained by providing a method and drug form wherein nasal, buccal, sublingual and vaginal absorption of poorly absorbed drugs is enhanced. The method comprises the steps of preparing a drug form suitable for nasal, buccal, sublingual or vaginal delivery, and a dosage form comprising an effective unit dosage amount of the poorly absorbed drug agents, an acylcarnitine absorption-enhancing agents or pharmaceutically acceptable salt thereof, the agent being present in said dosage form in an amount sufficient to be effective in enhancing the rate and extent of the nasal, buccal, sublingual and vaginal absorption of the therapeutic agent, and pharmaceutically acceptable excipients.

DETAILED DESCRIPTION OF THE INVENTION

The present invention, generally comprises the steps of preparing a drug form capable of being administered in the nasal, buccal, sublingual or vaginal compartment, wherein the drug form comprises an effective unit dosage amount of a poorly absorbed drug and an acylcarnitine absorption enhancing agent, the acylcarnitine agent being present in the drug form in a sufficient quantity to be effective in enhancing nasal, buccal, sublingual and vaginal drug absorption rates and administering the drug form to warm-blooded animals. The amount of poorly absorbed drug varies over a wide range, but generally the therapeutically effective unit dosage amount of the selected poorly absorbed drug depends on that amount known in the art to obtain the desired results.

The compounds that are used as absorption enhancers in our method and drug forms are acylcarnitines which are β-acyloxy derivatives of γ-trimethylaminobutyric acid and pharmaceutically acceptable salts thereof of the formula:

[(CH$_3$)$_3$N$^+$CH$_2$CH(OCOR)CH$_2$CO$_2$H]X$^-$ wherein R is:

(A) C$_2$–C$_{20}$ alkyl such as acetylcarnitine, hexanoylcarnitine, octanoylcarnitine, lauroylcarnitine, myristoylcarnitine, palmitoylcarnitine, stearoylcarnitine and the like;

(B) C$_2$–C$_{20}$ alkenyl with 1 to 6 double bonds such as 2-hexenoylcarnitine, 9-decenoylcarnitine, 9-hexadecenoylcarnitine (palmitoleoylcarnitine), oleoylcarnitine, myristoleoylcarnitine, 9,12-hexadecadienoylcarnitine, α-linoleoylcarnitine, α-linolenoylcarnitine, arachidoylcarnitine and the like;

(C) C$_2$–C$_{20}$ hydroxyalkyl with 1 to 3 hydroxy groups such as 2-hydroxylauroylcarnitine, 2-hydroxymyristoylcarnitine, 2-hydroxypalmitoylcarnitine and the like;

(D) C$_4$–C$_{20}$ ketoalkyl such as 6-ketodecanoylcarnitine, 4-keto-9,11,13-octadecatrienoylcarnitine and the like;

(E) C$_5$–C$_{20}$ hydroxyalkenyl such as 12-hydroxy-12-octadecenoylcarnitine;

(F) C$_5$–C$_{20}$ carbalkoxyalkyl such as ω-ethoxycarbonyloctanoylcarnitine and the like;

(G) Arylalkyl (C$_7$–C$_{20}$) such as phenylacetylcarnitine and the like;

(H) Alkylaryl (C$_7$–C$_{20}$) such as butylbenzoylcarnitine and the like;

(I) Carboxyalkyl (C$_5$–C$_{20}$) such as sebacylcarnitine, and where X is a pharmaceutically acceptable counterion such as chloride, sulfate, nitrate, perchlorate, bromide, phosphate, acetate, benzoate, tartrate, citrate, propionate, gluconate, lactate, maleate, fumarate, bezylate, camsylate, esylate, gluceptate, mesylate, napsylate and the like.

The most preferred nasal, buccal, sublingual and vaginal absorption enhancing vehicles of the above formula are:
1. Acetylcarnitine
2. Hexanolycarnitine
3. Lauroylcarnitine
4. Octanoylcarnitine
5. Myristoylcarnitine
6. Palmitoylcarnitine
7. Stearoylcarnitine
8. 2-Hexenoylcarnitine
9. 9-Decenoylcarnitine
10. 9-Hexadecenoylcarnitine
11. α-Linoleoylcarnitine
12. 2-Hydroxylauroylcarnitine
13. 2-Hydroxymyristoylcarnitine
14. 6-Keto-decanoylcarnitine
15. 12-Hydroxy-12-octadecenoylcarnitine
16. ω-Ethoxylcarbonyloctanoylcarnitine
17. 2-Hydroxypalmitoylcarnitine
18. Decanoylcarnitine.

Specific absorption enhancing vehicles useful in our method and drug forms are:
1. Acetylcarnitine
2. Hexanolycarnitine
3. Octanoylcarnitine
4. Decanoylcarnitine
5. Lauroylcarnitine
6. Myristoylcarnitine
7. Palmitoylcarnitine
8. Stearolycarnitine.

Various active agents provide beneficial effects when administered to patients. Such agents which can be made more useful by enhancing its absorption in accordance with this invention, are exemplified by, but not limited to, the following classes of agents:

(1) β-lactum antibiotics such as cefoxitin, N-formamidinylthienamycin, amoxicillin, ampicillin, azlocillin, bacampicillin, carbenicillin, cefaclor, cefadroxil, cefamandole, cefaparole, cefatrizine, cefazoline, cefonicid, cefaperazone, ceforanide, cefotaxime, cefotiam, cefroxadine, cefsulodin, ceftazidime, ceftizoxime, cephalaxin, cephaloglycin, cephaloridine, cephradine, cyclacillin, cloxacillin, dicloxacillin, floxacillin, hetacillin, methicillin, nafcillin, oxacillin, sarmoxacillin, sarpicillin, talampicillin, ticaricillin, penicillin G, penicillin V, pivampicillin, piperacillin, pirbenicillin and the like.

(2) Aminoglycoside antibiotics such as gentamycin, amikacin, astromicin, betamicin, butikacin, butirosin, clindamycin, josamycin, kanamycin, neomycin, netilmicin, tobramycin and the like.

(3) Antiviral agents such as ara C (cytarabine), acyclovir, floxuridine, ribavirin, vidarabine, idoxuridine, trifluridine and the like.

(4) Amino acids such as methyldopa, carbidopa, levodopa, fludalanine and the like.

(5) Muscle relaxants such as theophylline, cyclobenzaprine, aminophylline, diphylline, oxtriphylline, ambuphylline, fenethylline, guathylline, pentoxyfylline, xanthinol niacinate, theophylline glycinate, glucophylline and the like.

(6) Polypeptides such as cyclo(N-Me-Ala-Tyr-D-Trp-Lys-Val-Phe)acetate, somatostatin, atrial natriuretic factor, insulin, gastrin, caerulein, cholecystokinin and the like.

(7) Anti-inflammatory agents such as indomethacin, sulindac, ibuprofen and the like.

(8) Diuretics such as aldactone, hydrochlorothiazide, amiloride and the like.

The enhancement of drug absorption in accordnace with this invention is not by any means limited to the above drugs, but are in general applicable to other classes of drugs such as analgesics, anabolics, androgens, anorexics, adrenergics, antiadrenergics, antiallergics, antibacterials, anticholinergics, antidepressants, antidiabetics, antifungal agents, antihypertensives, antineoplastics, antipsychotics, sedatives, cardiovascular agents, antiulcer agents, anticoagulants, anthelmintics, radio-opaques, radio-nuclide diagnostic agents and the like.

For nasal administration, the formulations may be prepared as drops, sprays, mists, aerosols, gels, and other standard procedures known in the art. The preferred formulation is a liquid drop composed of a minimum of 1 mg acylcarnitine with the pharmacologically required dose of drug and sufficient excipients to formulate an acceptable composition. For buccal and sublingual application, the formulations may be prepared as gels, suspensions, polymers, tablets, and other standard procedures known in the art. The preferred formulation is a compressed tablet composed of a minimum of 1 mg acylcarnitine with the pharmacologically required dose of drug and sufficient excipients to formulate an acceptable composition. For vaginal administration, the formulations may be prepared as solutions, suspensions, gels, suppositories, tablets, and other standard procedures known in the art. The preferred formulation is a solid suppository composed of a minimum of 1 mg acylcarnitine ester with the pharmacologically required dose of drug and sufficient suppository base to formulate an acceptable composition. The methods and choice of excipients and suppository bases are well known to those skilled in the art and the composition of said formulations is not limited to liquid drops, compressed tablets, or solid suppositories by this invention.

Generally, the amount of adjuvant employed in the practice of the invention ranges from 0.05–500 mg in each unit dose. The percentage of adjuvant in the total combination of drug plus adjuvant is 0.05–50% with a preferred ratio of adjuvant in the total combination of adjuvant plus drug being 0.05–25%.

The following examples illustrate preparation of various compositions of the invention. The examples should be construed as illustrations rather than limitations thereof.

EXAMPLE 1

Effect of palmitoylcarnitine chloride on the nasal, buccal and vaginal absorption of α-methyldopa (amino acid, antihypertensive). Experiments were performed with rats wherein each animal received an aqueous formulation administered to the nasal, oral or vaginal cavities. The formulations contained the indicated amount of α-methyldopa in the presence or absence of 1.0 mg palmitoylcarnitine chloride. Procedures were tested to eliminate the possibility of cross-contamination between the nasal and oral cavities. Blood levels of α-methyldopa were determined by high performance liquid chromatography and the amount of drug absorbed (percent bioavailability) calculated against intravenous α-methyldopa administration.

| Administration Route | Dose of α-methyldopa (mg) | Percent α-methyldopa Bioavailability in the Absence (−) or Presence (+) of Palmitoylcarnitine | |
|---|---|---|---|
| | | (−) | (+) |
| Nasal Cavity | 0.5 | 7 ± 1.1 | 52 ± 16.2 |
| Oral Cavity | 2.5 | 3 ± 0.7 | 10 ± 6.0 |
| Vaginal Cavity | 2.5 | 2 ± 1.0 | 100 ± 55.0 |

Values represent the mean ± SD for n = 3 determinations.

EXAMPLE 2

Effect of palmitoylcarnitine chloride on the nasal, buccal and vaginal absorption of cefoxitin (β-lactam antibiotic). Experiments were performed with rats wherein each animal received an aqueous formulation administered to the nasal, oral or vaginal cavities. The formulations contained 2.5 mg sodium cefoxitin in the presence or absence of 1.0 mg palmitoylcarnitine chloride. Procedures were tested to eliminate the possibility of cross-contamination between the nasal and oral cavities. Blood levels of cefoxitin were determined by high performance liquid chromatography and the amount of drug absorbed (percent bioavailability) calculated against intravenous cefoxitin administration.

| Administration Route | Percent Cefoxitin Bioavailability in the Absence (−) or Presence (+) of Palmitoylcarnitine | |
|---|---|---|
| | (−) | (+) |
| Nasal Cavity | 15 ± 9.3 | 73 ± 38.3 |
| Oral Cavity | 0.4 ± 0.6 | 9 ± 6.5 |
| Vaginal Cavity | 2 ± 3.8 | 21 ± 8.5 |

Values represent the mean ± SD for n = 3 determinations.

What is claimed is:

1. A pharmaceutical composition for enhancing nasal, buccal, sublingual and vaginal absorption of a formulation comprising a therapeutically effective dosage amount of an amino acid drug and an acylcarnitine absorption enhancing agent of the formula:

$$[(CH_3)_3N^+CH_2CH(OCOR)CH_2CO_2H]X^-$$

wherein R is alkyl ($C_2$–$C_{20}$), alkenyl ($C_2$–$C_{20}$) with 1 to 6 double bonds, hydroxyalkyl ($C_2$–$C_{20}$) with 1 to 3 hydroxy groups, ketoalkyl ($C_4$–$C_{20}$), hydroxyalkenyl ($C_5$–$C_{20}$), carboxyalkyl ($C_4$–$C_{20}$), carbalkoxyalkyl ($C_5$–$C_{20}$), arylalkyl ($C_7$–$C_{20}$), alkylaryl ($C_7$–$C_{20}$) or and X is a pharmaceutically acceptable counterion.

2. The composition of claim 1 further comprising pharmaceutically acceptable excipients.

3. A method of enhancing the rate of absorption of an amino acid drug administered to the nasal, buccal, sublingual or vaginal cavities, which comprises administering a composition comprising a therapeutically effective dosage amount of said drug and an acylcarnitine absorption enhancing agent formula:

$$[(CH_3)_3N^+CH_2CH(OCOR)CH_2CO_2H]X^-$$

wherein R is saturated alkyl ($C_2$–$C_{20}$), alkenyl ($C_2$–$C_{20}$) with 1 to 6 double bonds, hydroxyalkyl ($C_2$–$C_{20}$) with 1 to 3 hydroxy groups, ketoalkyl ($C_4$–$C_{20}$), unsaturated hydroxyalkenyl ($C_5$–$C_{20}$), carboxyalkyl ($C_4$–$C_{20}$), carbalkoxyalkyl ($C_5$–$C_{20}$), arylalkyl ($C_7$–$C_{20}$), alkylaryl ($C_7$–$C_{20}$), carbalkoxyalkyl ($C_5$–$C_{20}$) and X is a pharmaceutically acceptable counterion.

4. The composition of claim 1, wherein said amino acid is selected from the group consisting of methyldopa, carbidopa, levodopa and fludalamine and said acylcarnitine absorption enhancing agent is selected from the group consisting of acetylcarnitine, hexanoylcarnitine, lauroylcarnitine, decanoylcarnitine, octanoylcarnitine, myristoylcarnitine, palmitoylcarnitine, stearoylcarnitine, 2-hexenoylcarnitine, 9-decenoylcarnitine, 9-hexadecenoylcarnitine α-linoleoylcarnitine, 2-hydroxylauroylcarnitine, 2-hydroxymyristoylcarnitine, 6-ketodecanoylcarnitine, 12-hydroxy-12-octadecenoylcarnitine, ω-ethoxycarbonyloctanoylcarnitine and 2-hydroxypalmitoylcarnitine.

5. The composition of claim 4, wherein said amino acid is α-methyldopa, carbidopa or levodopa and said enhancing agent is acetylcarnitine, hexanoylcarnitine, octanoylcarnitine, decanoylcarnitine, lauroylcarnitine, myristoylcarnitine, palmitoylcarnitine and stearoylcarnitine.

6. The composition of claim 5, wherein said amino acid is α-methyldopa and said enhancing agent is palmitoylcarnitine.

7. The method of claim 3 wherein said amino acid is selected from the group consisting of methyldopa, carbidopa, levodopa and fludalamine and said acylcarnitine absorption enhancing vehicle is selected from the group consisting of acetylcarnitine, hexenoylcarnitine, lauroylcarnitine, decanoylcarnitine, octanoylcarnitine, myristoylcarnitine, palmitoylcarnitine, stearoylcarnitine, 2-hexenoylcarnitine, 9-decenoylcarnitine, 9-hexadecenoylcarnitine α-linoleoylcarnitine, 2-hydroxylauroylcarnitine, 2-hydroxymyristoylcarnitine, 6-ketodecanoylcarnitine, 12-hydroxy-12-octadecenoylcarnitine, ω-ethoxycarbonyloctanoylcarnitine and 2-hydroxypalmitoylcarnitine.

8. The method of claim 7, wherein said amino acid is methyldopa, carbidopa or levodopa; and said enhancing agent is hexenoylcarnitine, octanoylcarnitine, decanoylcarnitine, lauroylcarnitine, myristoylcarnitine, palmitoylcarnitine or stearoylcarnitine and pharmaceutically acceptable salts thereof.

9. The method of claim 8, wherein said amino acid is α-methyldopa and said enhancing agent is palmitoylcarnitine, lauroylcarnitine, myristoylcarnitine, or stearoylcarnitine.

10. The method of claim 9, wherein the enhancing agent is palmitoylcarnitine.

11. The method of claim 8, wherein said amino acid is α-methyldopa or levodopa and said enhancing agent is palmitoylcarnitine.

12. The method of claim 11, wherein said amino acid is α-methyldopa.

* * * * *